United States Patent
Schabbach et al.

(10) Patent No.: US 11,331,429 B2
(45) Date of Patent: May 17, 2022

(54) CARTRIDGE FOR DOSAGE SENSING

(71) Applicant: SANOFI, Paris (FR)

(72) Inventors: Michael Schabbach, Frankfurt am Main (DE); Alexander Allerdings, Frankfurt am Main (DE); Christoph Dette, Frankfurt am Main (DE); Martin Otten, Frankfurt am Main (DE); Christian Pommereau, Frankfurt am Main (DE); Dietmar Hammen, Frankfurt am Main (DE); Paul Edward Jansen, Boston, MA (US); Ulrich Brueggemann, Bridgewater, NJ (US)

(73) Assignee: Sanofi, Paris (FR)

( * ) Notice: Subject to any disclaimer, the term of this patent is extended or adjusted under 35 U.S.C. 154(b) by 249 days.

(21) Appl. No.: 16/609,796

(22) PCT Filed: May 2, 2018

(86) PCT No.: PCT/EP2018/061114
§ 371 (c)(1),
(2) Date: Oct. 31, 2019

(87) PCT Pub. No.: WO2018/202663
PCT Pub. Date: Nov. 8, 2018

(65) Prior Publication Data
US 2020/0054830 A1    Feb. 20, 2020

(30) Foreign Application Priority Data

May 5, 2017 (EP) .................................. 17305517

(51) Int. Cl.
*A61M 5/20* (2006.01)
*A61M 5/315* (2006.01)

(52) U.S. Cl.
CPC .......... *A61M 5/20* (2013.01); *A61M 5/31533* (2013.01); *A61M 5/31565* (2013.01);
(Continued)

(58) Field of Classification Search
CPC ................ A61M 5/20; A61M 5/31533; A61M 5/31565; A61M 5/31553; A61M 5/31568;
(Continued)

(56) References Cited

U.S. PATENT DOCUMENTS

| 5,720,733 A | * | 2/1998 | Brown ................ A61M 5/1782 222/23 |
| 2014/0303567 A1 | | 10/2014 | Qurishi et al. |
| 2015/0174342 A1 | * | 6/2015 | Mitrosky .......... A61M 5/31525 604/506 |

(Continued)

FOREIGN PATENT DOCUMENTS

| JP | 2013-505433 | 2/2013 |
| KR | 10-2016-0053322 | 5/2016 |

(Continued)

OTHER PUBLICATIONS

International Preliminary Report on Patentability in Application No. PCT/EP2018/061114, dated Nov. 5, 2019, 7 pages.

(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

An injection device is provided, comprising a cartridge configured to hold a volume of fluid, the cartridge having a proximal end and a distal end through which the fluid is dispensed; a first stopper disposed in the cartridge and configured to move from the proximal end toward the distal end to cause the fluid to be dispensed through the distal end of the cartridge; a second stopper disposed at the distal end (Continued)

of the cartridge, the second stopper including an aperture through which the fluid is dispensed; a reflector disposed at the distal end of the cartridge; and a transmitter and a receiver disposed in the first stopper, the transmitter configured to transmit one or more waves toward the reflector and the receiver configured to receive reflections of the one or more waves from at least the reflector.

18 Claims, 5 Drawing Sheets

(52) U.S. Cl.
CPC .............. *A61M 2205/3306* (2013.01); *A61M 2205/3375* (2013.01); *A61M 2205/3389* (2013.01)

(58) Field of Classification Search
CPC ............. A61M 2205/3306; A61M 2205/3375; A61M 2205/3389
See application file for complete search history.

(56) References Cited

U.S. PATENT DOCUMENTS

2017/0136185 A1* 5/2017 Rios .................. A61M 5/31511
2020/0164154 A1* 5/2020 Schabbach ............. G01F 22/00

FOREIGN PATENT DOCUMENTS

| WO | WO 2011/032960 | 3/2011 |
| WO | WO 2013/064590 | 5/2013 |
| WO | WO 2016/113409 | 7/2016 |
| WO | WO 2016/202339 | 12/2016 |
| WO | WO 2017/070391 | 4/2017 |

OTHER PUBLICATIONS

International Search Report and Written Opinion in Application No. PCT/EP2018/061114, dated Jun. 11, 2018, 10 pages.

* cited by examiner

CARTRIDGE FOR DOSAGE SENSING

CROSS REFERENCE TO RELATED APPLICATIONS

The present application is the national stage entry of International Patent Application No. PCT/EP2018/061114, filed on May 2, 2018, and claims priority to Patent Application No. EP 17305517.9, filed on May 5, 2017, the entire contents of which are hereby incorporated by reference.

TECHNICAL FIELD

This disclosure relates to an injection device, and more particularly, to a cartridge of an injection device for sensing a dosage of a medicament to be administered.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

SUMMARY

According to a first aspect, an injection device includes a cartridge configured to hold a volume of fluid. The cartridge has a proximal end and a distal end through which the fluid is dispensed. The injection device also includes a first stopper disposed in the cartridge and configured to move from the proximal end toward the distal end to cause the fluid to be dispensed through the distal end of the cartridge. The injection device also includes a second stopper disposed at the distal end of the cartridge. The second stopper includes an aperture through which the fluid is dispensed. The injection device also includes a reflector disposed at the distal end of the cartridge. The injection device also includes a transmitter and a receiver disposed in the first stopper. In some embodiments, the injection device may include a transceiver that includes the transmitter and the receiver. The transmitter is configured to transmit one or more waves (e.g., acoustic waves, optical waves, etc.) toward the reflector, and the receiver is configured to receive reflections of the one or more waves from at least the reflector.

In some embodiments, the cartridge may have a generally cylindrical shape that tapers into a cone shape at the distal end. The distal end of the cartridge may include a bottom surface that forms a 90° angle with a peripheral wall of the cartridge. The reflector may be disposed at the bottom surface such that the one or more waves are transmitted at normal incidence to the reflector. The reflector may comprise one or more of ceramic, metal, and biaxially-oriented polyethylene terephthalate (BoPET).

The cartridge may include a material (e.g., a transparent material such as glass or plastic) that allows the one or more waves and the reflections of the one or more waves to pass therethrough. The reflector may be embedded in the material at the distal end of the cartridge, disposed on an outer surface of the distal end of the cartridge, or disposed on an inner surface of the distal end of the cartridge.

The transmitter may be an acoustic transmitter (e.g., an ultrasonic transmitter) and the one or more waves may be acoustic waves (e.g., ultrasound waves). The transmitter may be an optical source and the one or more waves may be optical waves.

The reflector may be disposed on a surface of the second stopper. The second stopper may include a material that allows the one or more waves and the reflections of the one or more waves to pass therethrough, and the reflector may be embedded in the material of the second stopper.

Information related to the one or more transmitted waves and the reflections of the one or more waves may be used to determine the volume of the fluid in the cartridge. The volume of the fluid in the cartridge may be determined continuously during dispensing of the fluid. The fluid may be held in the cartridge, and the fluid may comprise a medicament.

According to a second aspect, an injection device includes a cartridge configured to hold a volume of fluid. The cartridge has a proximal end and a distal end through which the fluid is dispensed. The injection device also includes a first stopper disposed in the cartridge and configured to move from the proximal end toward the distal end to cause the fluid to be dispensed through the distal end of the cartridge. The injection device also includes a first electrode disposed in the first stopper. The injection device also includes a second stopper disposed at the distal end of the cartridge. The second stopper includes an aperture through which the fluid is dispensed. The injection device also includes a second electrode disposed in the second stopper. A voltage is applied across the first electrode and the second electrode, and a capacitance value related to the first electrode and the second electrode is indicative of a distance between the first stopper and the second stopper. In some embodiments, the volume of the fluid in the cartridge may be determined based on the distance between the first stopper and the second stopper.

DESCRIPTION OF DRAWINGS

Like reference symbols in the various drawings indicate like elements.

DETAILED DESCRIPTION

Figure 1A:
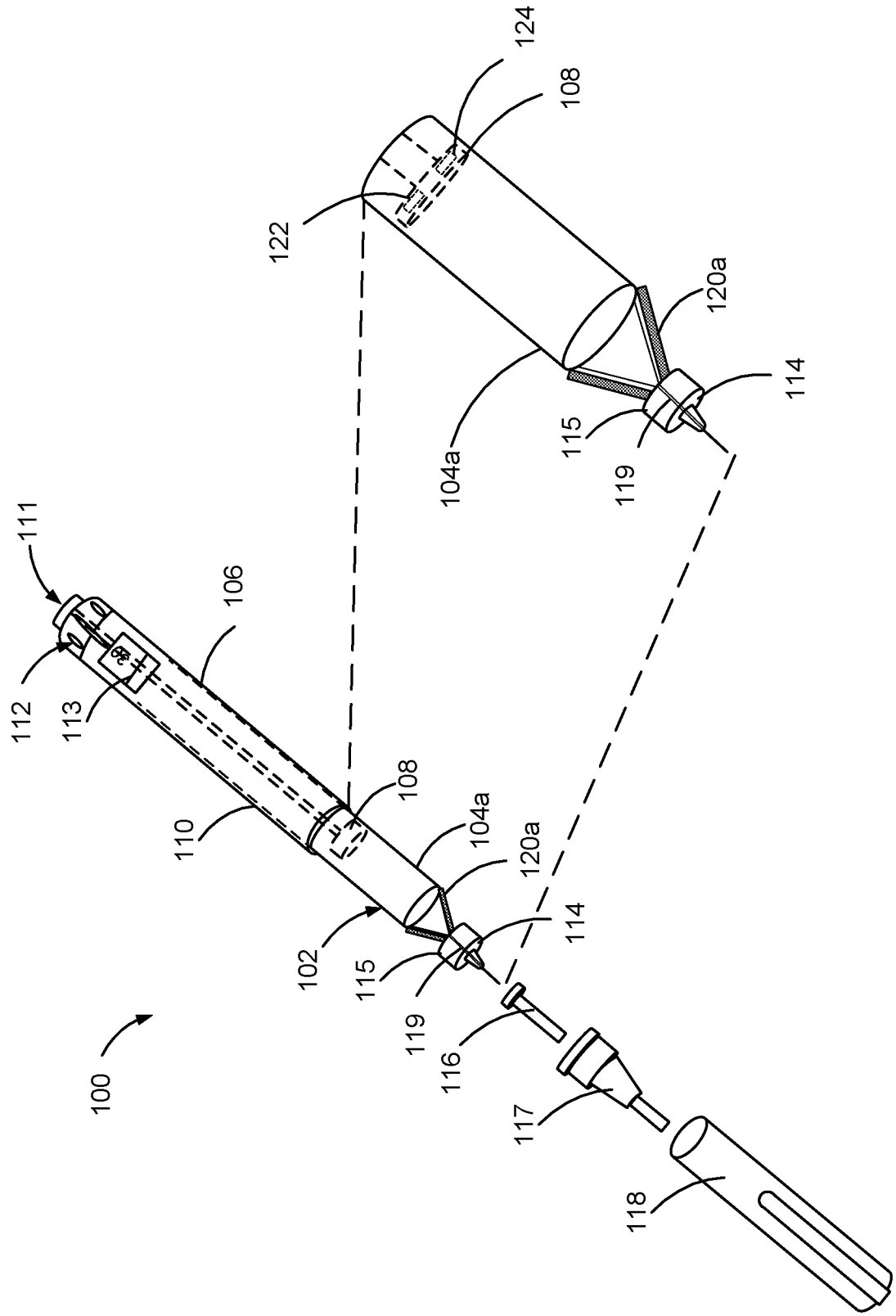
FIGS. 1A and 1B are exploded views of examples of an injection device that includes a reflector.

The subject matter described herein will largely be described with reference to a drug delivery device such as an injection device (e.g., an insulin injection device). However, the systems and techniques described herein are not limited to such applications, and may equally well be deployed with injection devices that eject other medicaments, or with other types of medical devices (e.g., pumps).

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

FIG. 1A is an exploded view of an example of an injection device 100. The injection device 100 may be a pre-filled, disposable or reusable injection pen. The injection device 100 includes a housing 110 that contains a cartridge 102. The cartridge 102 is configured to hold a volume of fluid. In some embodiments, the cartridge 102 is a medicament container, such as an insulin container. The cartridge 102 includes a distal end 104a and a proximal end 106. In some embodiments, the proximal end 106 of the cartridge 102 may reside within the housing 110 of the injection device 100 and therefore may not be readily visible.

The injection device 100 includes a first stopper 108 that is disposed in the cartridge 102. The first stopper 108 may be connected to a piston (e.g., a plunger arm), and the first stopper and the piston may collectively form a drive mechanism that is configured to cause the fluid to be ejected from the cartridge 102. For example, the piston is configured to cause the first stopper 108 to move from the proximal end 106 of the cartridge 102 toward the distal end 104a of the cartridge 102 to cause the fluid to be dispensed through the distal end 104a of the cartridge 102. The injection device 100 also includes a second stopper 115 that is disposed at the distal end 104a of the cartridge 102. The second stopper 115 includes an aperture 119 through which the fluid is dispensed. A needle 114 can be affixed to the second stopper 115 proximate to the aperture 119 such that the fluid travels through the aperture 119 and the needle 114 when dispensed. In some embodiments, the second stopper 115 and the needle 114 are threaded such that the needle 114 can be screwed onto the second stopper 115 or the second stopper 115 can be screwed onto the needle 114. The needle 114 is protected by an inner needle cap 116 and an outer needle cap 117, which in turn can be covered by a cap 118.

A drug dose (e.g., such as an insulin dose) to be ejected from injection device 100 can be selected by turning a dosage knob 112, and the selected dose can then be displayed by a dosage window 113. In some examples, the dosage window 113 is a display, such as an electronic display. In some examples, the selected dose can be displayed in multiples of International Units (IU), wherein one IU is the biological equivalent of about 45.5 micrograms of pure crystalline insulin (e.g., 1/22 mg). An example of a selected dose displayed in the dosage window 113 may, for example, be 30 IUs, as shown in FIG. 1A. In some examples, the selected dose may be displayed differently, for example, by an electronic display. In some examples, the dosage window 113 relates to the section of the injection device through or on which the selected dosage is visible.

Turning the dosage knob 112 may cause a mechanical click sound to provide acoustical feedback to a user. The numbers displayed in the dosage window 113 are printed on a sleeve that is contained in housing 110 and mechanically interacts with a piston in the cartridge 102. When the needle 114 is inserted into a skin portion of a patient, and then an injection button 111 is pushed, the medicament is ejected from the injection device 100. Ejection of the dose may also cause a mechanical click sound. Such a mechanical click sound may be different from the sounds produced when the dosage knob 112 is turned.

The injection device 100 may be used for several injection processes until either the cartridge 102 is empty or the expiration date of the injection device 100 (e.g., 28 days after the first use) is reached. In some examples, before using the injection device 100 for the first time, it may be necessary to perform a "prime shot" to remove air from the cartridge 102 and the needle 114, for example, by selecting two units of medicament and pressing the injection button 111 while holding the injection device 100 with the needle 114 oriented upwards.

The injection device 100 is configured to determine the volume of medicament fluid (e.g., insulin) in the cartridge 102, which can represent the dosage of medicament to be administered to the patient. For example, the injection device includes a transmitter 122 and a receiver 124 that are disposed in the first stopper 108. In some embodiments, one or both of the transmitter 122 and the receiver 124 may be positioned elsewhere on the first stopper 108, such as embedded in the first stopper 108. The transmitter 122 is configured to transmit one or more waves (e.g., acoustic waves, optical waves, etc.) toward the distal end 104a of the cartridge 102. The one or more waves are reflected from the distal end 104a of the cartridge 102 (e.g., by bouncing off a surface of the cartridge 102 and/or a reflector, as described in detail below). The receiver 124 is configured to receive reflections of the one or more waves. Information related to the one or more transmitted waves and the reflections of the one or more transmitted waves can be used to determine the volume of the fluid in the cartridge 102. For example, the information related to the one or more transmitted waves and the reflections of the one or more waves can be used to determine a distance traveled by the one or more waves, the distance traveled by the one or more waves can be used to determine a volume of the fluid in the cartridge, and the volume of the fluid in the cartridge can be used to determine a dose of medicament to be administered to a patient. In some embodiments, both the transmitter 122 and the receiver 124 are included as components of a single transceiver package.

In some embodiments, the information related to the one or more transmitted waves (e.g., times of transmission) and the reflections of the one or more transmitted waves (e.g., times of receipt) is provided to and/or received by a computing device (e.g., the computer system 300 of FIG. 3), and the computing device uses such information to determine the volume of the fluid in the cartridge 102. In some examples, the transmitter 122 is an acoustic (e.g., ultrasonic) transmitter that is configured to transmit one or more acoustic waves (e.g., ultrasonic waves) toward the distal end 104a of the cartridge 102, and the receiver 124 is an acoustic receiver that is configured to receive reflections of the one or more acoustic waves. The computing device can identify times at which each acoustic wave is transmitted, and for each transmitted acoustic wave, times as which the corresponding reflection is received by the receiver 124. With the acoustic wave velocity being known (e.g., in this case, the speed of sound), the elapsed time between transmission and receiving of the wave, sometimes referred to as time of flight (TOF), can be used to determine the distance traveled by the wave. The distance traveled by the wave represents the distance from the transmitter 122, to the reflection surface (e.g., at the distal end 104a of the cartridge 102), to the receiver 124. This distance can be divided by two to determine the distance between the first stopper 108 and the reflection surface. Because the reflection surface is at the distal end 104a of the cartridge 102, the determined distance represents a length of the cartridge 102 within which the fluid resides. The determined distance, along with the known dimensions of the cartridge 102, can be used to determine the volume of the fluid in the cartridge 102.

In an example, the transmitter 122 transmits an acoustic wave at a first time $t_1$. The first time $t_1$ (e.g., the transmission time of the acoustic wave) is provided to the computing device. The acoustic wave propagates from the transmitter 122 toward the distal end 104a of the cartridge 102 and is reflected off of (e.g., bounces off of) a reflector 120a. A reflection of the acoustic wave (e.g., a reflected wave) propagates from the distal end 104a of the cartridge 102 toward the receiver 124. The reflected wave is received at a second time $t_2$. The speed of the acoustic wave is the speed of sound in liquid. The elapsed time between transmission and receiving of the acoustic wave is $t_2-t_1$. The elapsed time is multiplied by the speed of sound to determine the distance traveled by the wave from the transmitter 122, to the distal end 104a of the cartridge 102, back to the receiver 124. The distance traveled is divided by two to determine the distance between the transmitter 122/the receiver 124 and the distal end 104a of the cartridge 102. The volume of fluid in the cartridge 102 (e.g., the volume of fluid enclosed in the cartridge 102 between the first stopper 108 and the distal end 104a) is determined by multiplying the determined distance by the cross-sectional area of the cartridge 102. The determined volume of fluid in the cartridge 102 is the dose that is to be administered to the patient.

In some embodiments, the injection device 100 includes the reflector 120a that is disposed at the distal end 104a of the cartridge 102. The distal end 104a of the cartridge 102 is sometimes referred to as the shoulder of the cartridge 102. The reflector 120a is configured to improve the signal quality of the reflected waves (e.g., by minimizing signal loss upon reflection, reducing noise in the signal, improving signal to noise ratio, etc.), thereby improving the TOF calculation. In the illustrated example, the reflector 120a is disposed on an outer surface of the distal end 104a of the cartridge 102. In this way, the reflector 120a may be applied to the cartridge 102 after manufacture of the cartridge 102. In some embodiments, including the reflector 120a on an outer surface of the distal end 104a of the cartridge 102 serves to avoid any potential issues with the material of the reflector 120a introducing contaminants to the medicament. The cartridge 102 may be generally cylindrically shaped. In the illustrated example, the cartridge 102 tapers into a cone shape at the distal end 104a. The reflector 120a may be wrapped around the outer surface of the cone-shaped portion of the distal end 104a of the cartridge 102. The cartridge 102 may be made from and/or include a material that allows the one or more waves and the reflections of the one or more waves to pass therethrough (or, e.g., pass substantially therethrough). The transmitter 122 is configured to transmit the one or more waves toward the reflector 120a, and the receiver 124 is configured to receive reflections of the one or more waves from at least the reflector 120a.

The reflector 120a may be made from and/or include a material that promotes reflection of the particular types of waves being transmitted. In some examples, the reflector 120a may include a material that has a relatively smooth surface such as ceramic to minimize the occurrence of wayward reflections that may otherwise occur due to variations and/or defects in the surface geometry. In some examples, the reflector 120a may include a material that has a relatively high reflectance, such as metal and/or biaxially-oriented polyethylene terephthalate (BoPET). Such materials may improve signal quality and/or reduce losses that may otherwise occur upon reflection, thereby resulting in a TOF measurement—and in turn, a distance calculation—that is representative of the true distance between the transmitter 122/receiver 124 (e.g., the first stopper 108) and the reflector 120a. The improved accuracy of the distance calculation in turn leads to an even more accurate volume calculation.

In some examples, the reflector 120a may be embedded in the material of the cartridge 102. For example, the reflector 120a may be embedded between layers (e.g., plastic or glass layers) of the cartridge 102. For example, the reflector 120a may be a film that is disposed between layers of the cone-shaped portion of the distal end 104a of the cartridge 102. In some examples, the reflector 120a may be disposed on an inner surface of the cartridge 102. For example, the reflector 120a may be a film within the cartridge 102 that is applied on an inner surface of the cone-shaped portion of the distal end 104a of the cartridge 102. In some examples (e.g., examples in which the reflector 120a is disposed inside the cartridge 102), the reflector 120a may be made from a material that does not compromise the medicament. The reflector 120a may be made from a material that is biocompatible.

Figure 1B:
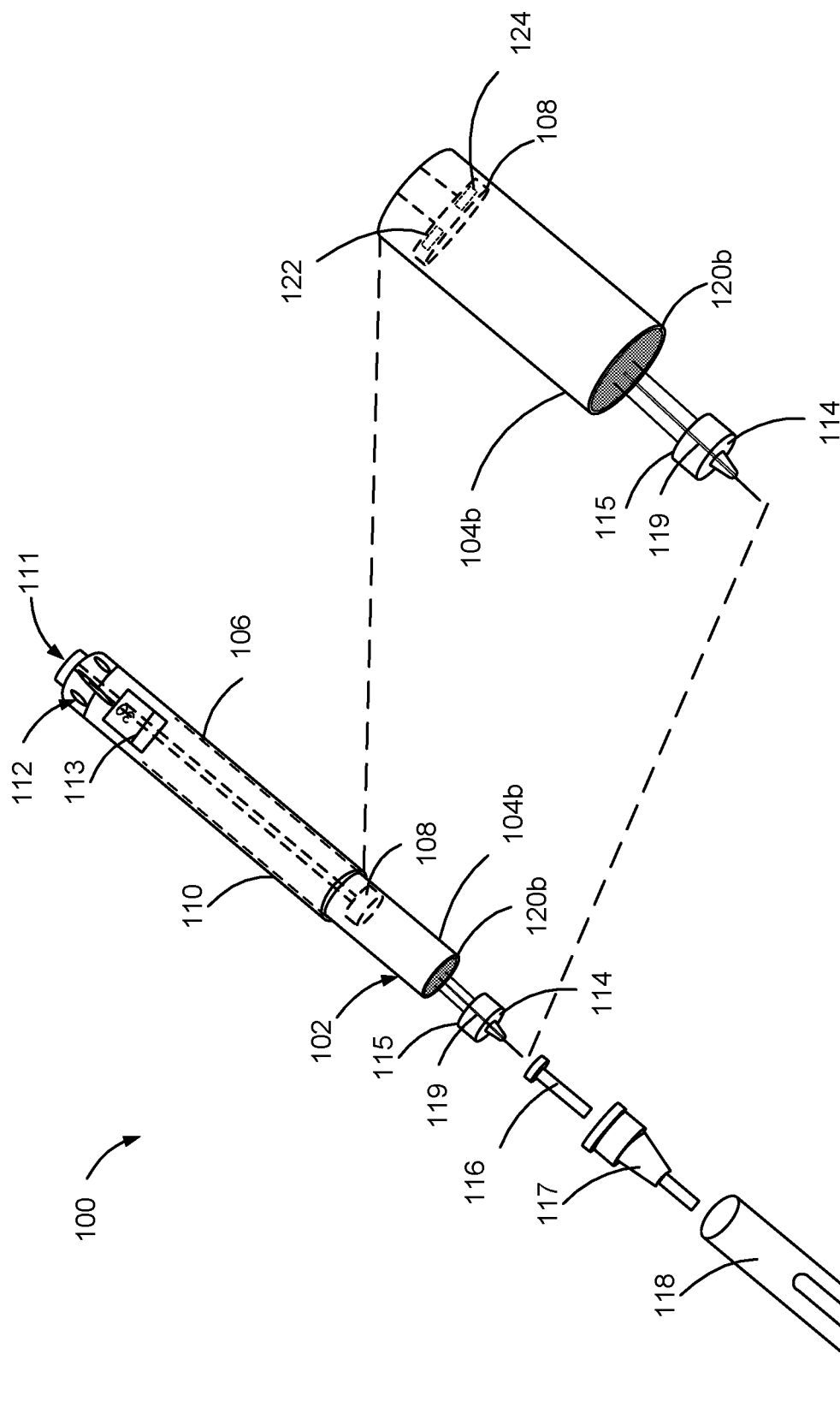

In some examples, the injection device 100 may include one or more other features that can further improve the accuracy of the distance and volume calculations. FIG. 1B shows another exploded view of an example of the injection device 100. In this example, the cartridge 102 includes a distal end 104b that has a bottom surface that forms a 90° angle (or, e.g., an angle of approximately 90°) with a peripheral wall of the cartridge 102. The injection device 100 includes a reflector 120b that is disposed at the bottom surface of the distal end 104b such that the one or more waves are transmitted at normal incidence to the reflector 120b. As such, the transmitted waves can be reflected directly back to the receiver 124 in a direction normal to the transmitter 122 and receiver 124 (e.g., in a direction that is perpendicular to the bottom surface of the first stopper 108). The normal incidence of the transmitted waves and the normal incidence of the reflections of the waves allows for determination of a TOF measurement that can be used to obtain an accurate distance measurement (e.g., between the first stopper 108 and the reflector 120b), and in turn, an accurate medicament volume measurement.

The reflector 120b may be substantially similar to the reflector 120a described above with respect to FIG. 1A in terms of the materials used for the reflector 120b and/or the operation of the reflector 120b. While the reflector 120b is disposed on an outer surface of the distal end 104b of the cartridge 102 in the illustrated example, in some embodiments, the reflector 120b may be embedded in the material of the cartridge 102 or disposed on an inside surface of the bottom surface of the distal end 104b of the cartridge 102, as previously described.

In some embodiments, the accuracy of the distance and volume calculations can be improved by shaping the distal end 104b of the cartridge 102 as shown in FIG. 1B. For example, the injection device 100 may include the distal end 104b that has a bottom surface that forms a 90° angle (or, e.g., an angle of approximately 90°) with the peripheral wall of the cartridge 102 without also including the reflector 120b. In this way, the accuracy of the distance and volume calculations can be sufficiently improved due to the shape of the distal end 104b of the cartridge 102 without requiring the reflector 120b.

Figure 1C:
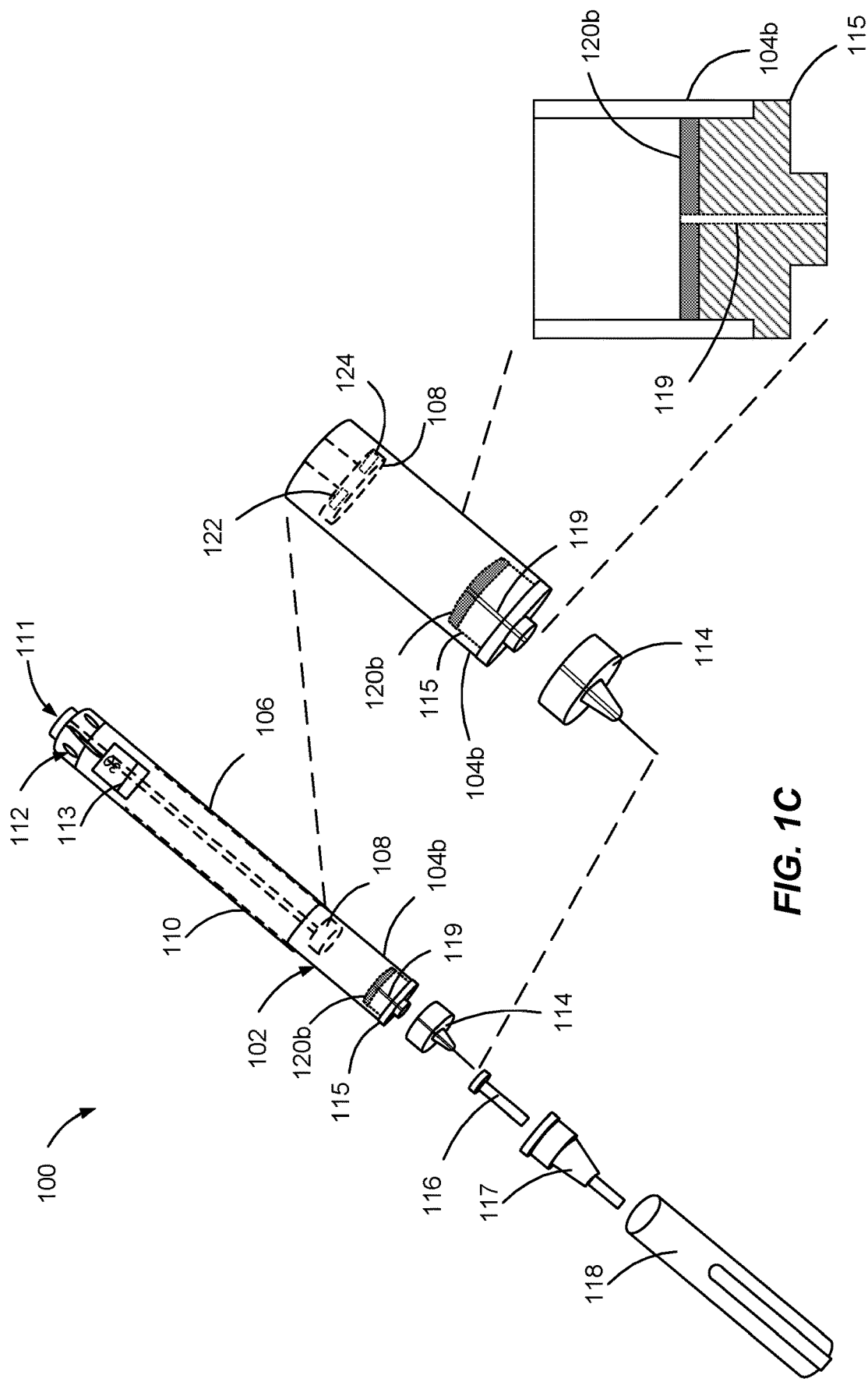
FIG. 1C is an exploded view and a cross-sectional view of an example of an injection device that includes a reflector.

FIG. 1C shows another exploded view and a cross-sectional view of an example of the injection device 100. In this example, the reflector 120b is disposed on a surface of the second stopper 115. While the reflector 120b is disposed on a surface of the second stopper 115 in the illustrated example, in some embodiments, the reflector 120b may be embedded in the material of the second stopper 115. In some examples (e.g., examples in which the reflector 120b is embedded in the second stopper 115), the second stopper 115 may include a material that allows the one or more waves and the reflections of the one or more waves to pass therethrough (or, e.g., pass substantially therethrough).

Referring generally to FIGS. 1A-1C, in some embodiments, the transmitter 122 is an optical source (e.g., a light source) that is configured to transmit one or more optical waves (e.g., light waves) toward the reflector 120a, 120b, and the receiver 124 is an optical receiver that is configured to receive reflections of the one or more optical waves. In some examples (e.g., examples in which the reflector 120a, 120b is disposed outside of the cartridge 102 or embedded in the material of the cartridge 102), the cartridge 102 may be made from and/or include a material that allows the one or more optical waves and the reflections of the one or more optical waves to pass therethrough (or, e.g., pass substantially therethrough). In some embodiments, the cartridge 102 includes a transparent material, such as one or both of glass and plastic. In some examples (e.g., examples in which the reflector 120b is embedded in the material of the second stopper 115), the second stopper 115 may also be made from and/or include a material that allows the one or more optical waves and the reflections of the one or more optical waves to pass therethrough (or, e.g., pass substantially therethrough). In some embodiments, the second stopper 115 includes a transparent material, such as one or both of glass and plastic.

While the injection device 100 has been largely described as being configured to determine the volume of the fluid in the cartridge 102 using information related to the one or more transmitted waves and the reflections of the one or more waves, in some embodiments, the injection device 100 may include one or more components other than or in addition to the transmitter 122 and receiver 124 for determining the volume of the fluid.

While the transmitter 122 and the receiver 124 have largely been described as being disposed in the first stopper 108, in some embodiments, the transmitter 122 and the receiver 124 may be positioned elsewhere. For example, in some embodiments, the transmitter 122 and the receiver 124 may be positioned at the distal end 104b of the cartridge 102 (e.g., at the second stopper 115). Similarly, while the reflectors 120a, 120b have largely been described as being positioned at the distal end 104b of the cartridge 102, in some embodiments, the reflectors 120a, 120b may be positioned elsewhere, such as at the first stopper 108.

Figure 2:
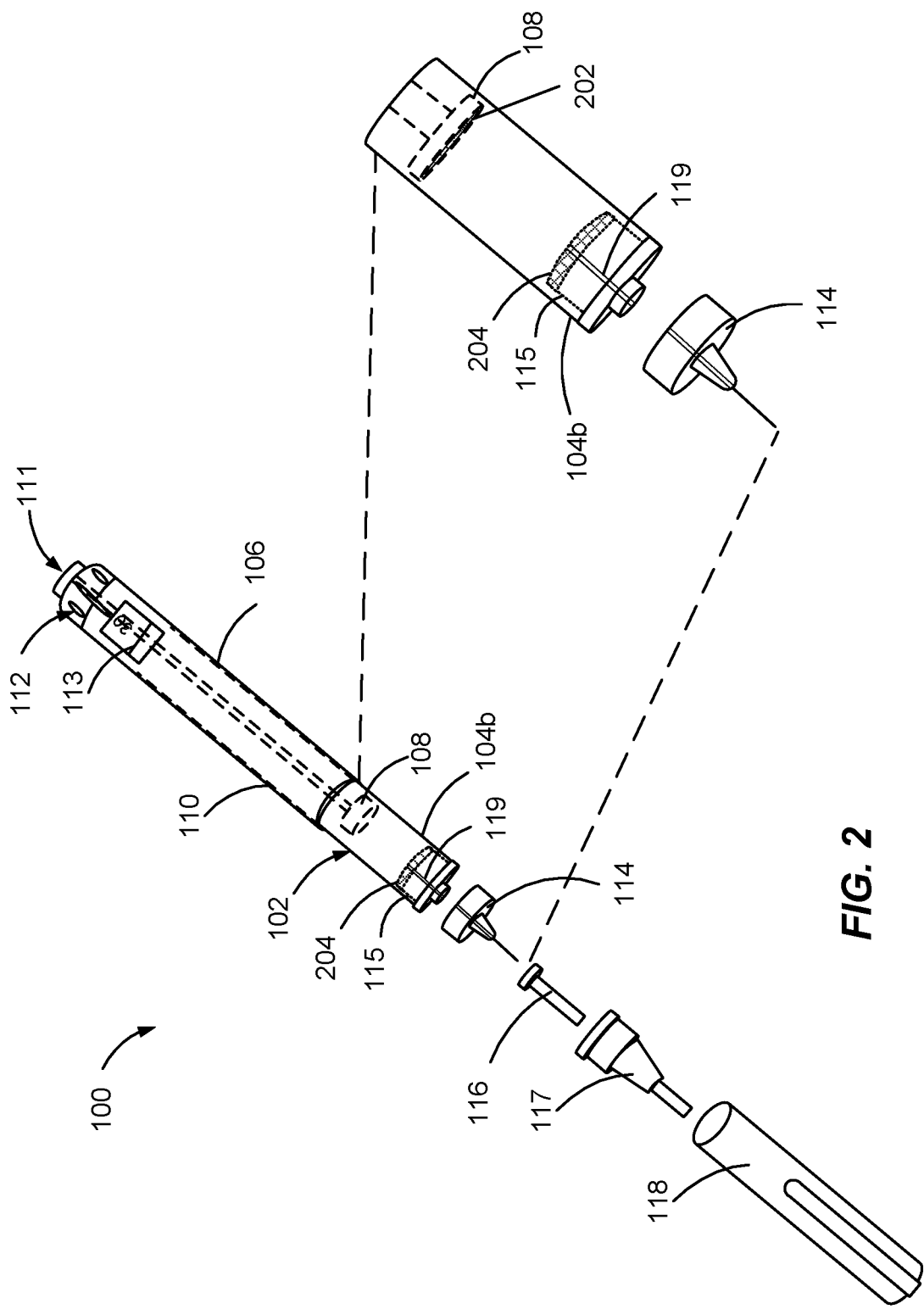
FIG. 2 is an exploded view of an example of an injection device that includes electrodes.

FIG. 2 shows another exploded view of the injection device 100. In this example, the injection device 100 is configured to determine the volume of the fluid in the cartridge 102 using a capacitive sensing technique. The injection device 100 includes a first electrode 202 that is disposed in the first stopper 108 and a second electrode 204 that is disposed in the second stopper 115. The electrodes 202, 204 form a capacitor with the medicament fluid between the electrodes 202, 204 acting as a dielectric. The electrodes 202, 204 can be powered by electronics of the injection device 100. For example, electrical power can be provided to the first electrode 202 and the second electrode 204 such that a voltage is applied across the first electrode 202 and the second electrode 204. A capacitance value related to the electrodes 202, 204 is generated based on at least a distance between the electrodes 202, 204. In other words, the capacitance of the electrodes 202, 204 changes as the electrodes 202, 204 move closer together (e.g., as the first stopper 108 approaches the second stopper 115).

The capacitance value may be indicative of (e.g., proportional to) the distance between the electrodes 202, 204. In some embodiments, the capacitance value may be provided to and/or received by a computing device (e.g., the computer system 300 of FIG. 3), and the computing device can use the capacitance value to determine the distance between the first stopper 108 and the second stopper 115. The determined distance represents a length of the cartridge 102 within which the fluid resides. The determined distance, along with the known dimensions of the cartridge 102, can be used to determine the volume of the fluid in the cartridge 102.

In some embodiments, the volume of the fluid in the cartridge 102 may be determined continuously as the fluid is dispensed from the injection device 100. For example, when the injection button 111 is pushed and as the medicament is ejected from the cartridge 102, the injection device 100 may continuously determine the volume of the fluid in the cartridge 102 such that the user can receive continuous feedback of the current volume of fluid in the cartridge 102.

In particular, in a manner substantially similar to that described above with respect to FIG. 1A, information related to one or more transmitted waves (e.g., times of transmission) and the reflections of the one or more transmitted waves (e.g., times of receipt) can be provided to and/or received by the computing device. The elapsed time between transmission and receiving of the wave (e.g., the TOF) can be multiplied by the speed of the wave (e.g., the speed of sound) to determine the distance traveled by the wave. The distance traveled by the wave represents the distance from the transmitter 122, to the distal end 104a of the cartridge 102, and back to the receiver 124. The distance traveled is divided by two to determine the distance between the transmitter 122/the receiver 124 and the distal end 104a of the cartridge 102. The volume of fluid in the cartridge 102 (e.g., the volume of remaining fluid enclosed in the cartridge 102 between the first stopper 108 and the distal end 104a) is determined by multiplying the determined distance by the cross-sectional area of the cartridge 102. The determined volume of fluid in the cartridge is the dose that is remaining in the cartridge 102 which is yet to be administered to the patient. The volume of fluid in the cartridge 102 can be continuously determined such that the remaining dosage is known throughout administration.

Figure 3:
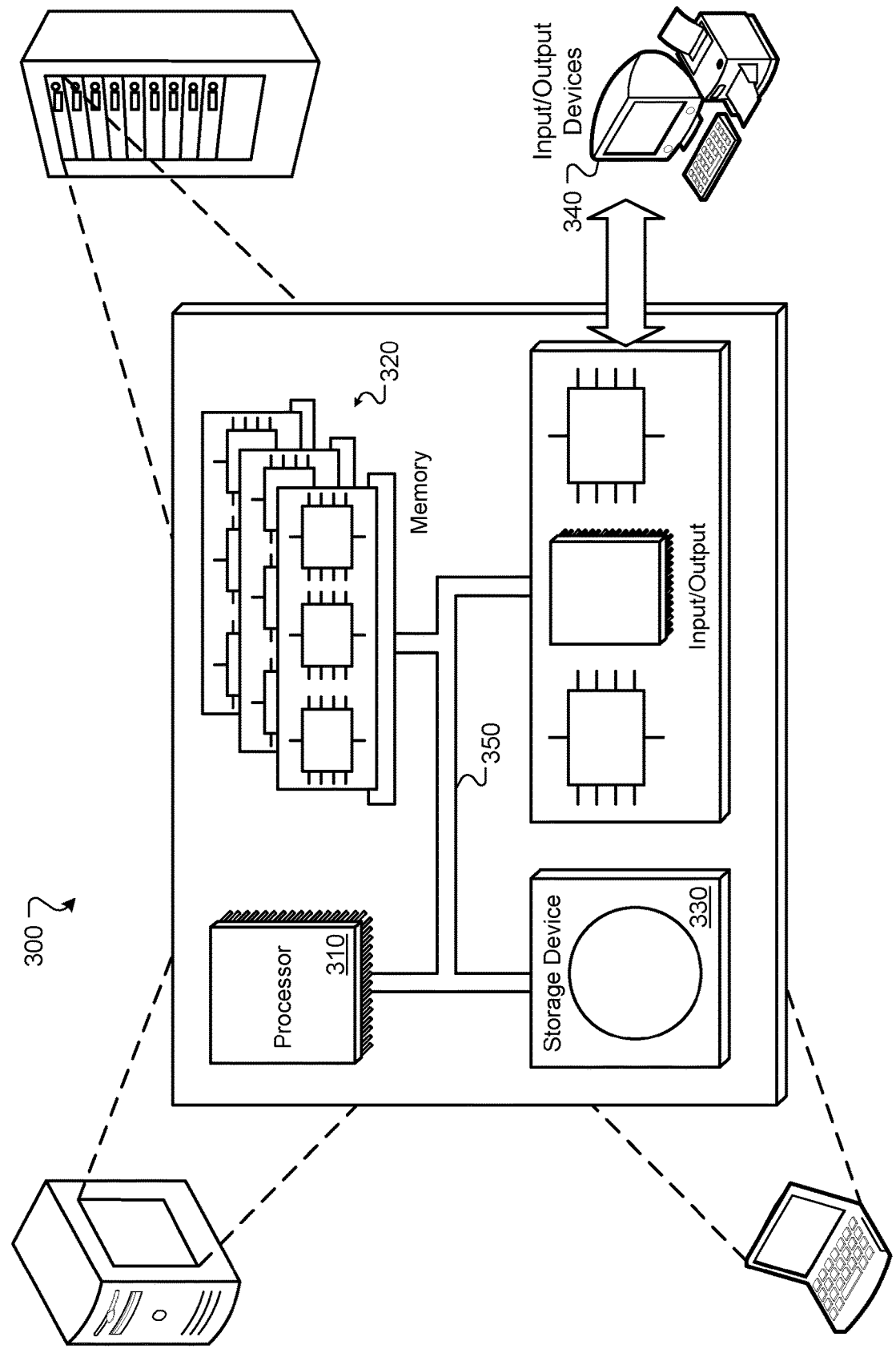
FIG. 3 is a block diagram of an example computer system.

FIG. 3 is a block diagram of an example computer system 300. For example, the computer system 300 may be incorporated into the injection device 100 of FIGS. 1A-1C and 2, and/or the injection device 100 may be configured to interact with a separate computer system 300. The system 300 includes a processor 310, a memory 320, a storage device 330, and an input/output device 340. Each of the components 310, 320, 330, and 340 can be interconnected, for example, using a system bus 350. The processor 310 is capable of processing instructions for execution within the system 300. The processor 310 can be a single-threaded processor, a multi-threaded processor, or a quantum computer. The processor 310 is capable of processing instructions stored in the memory 320 or on the storage device 330. The processor 310 may execute operations such as causing the injection device 100 to carry out one or more of the operations described above to determine the volume of the fluid in the cartridge 102.

The memory 320 stores information within the system 300. In some embodiments, the memory 320 is a computer-readable medium. The memory 320 can, for example, be a volatile memory unit or a non-volatile memory unit. In some embodiments, the memory 320 stores information related to one or more of the velocity of the one or more waves transmitted by the transmitter 122, the dimensions of the cartridge 102, and data that can be used to correlate the applied voltage across the electrodes 202, 204 to a distance between the electrodes 202, 204.

The storage device 330 is capable of providing mass storage for the system 300. In some embodiments, the storage device 330 is a non-transitory computer-readable medium. The storage device 330 can include, for example, a hard disk device, an optical disk device, a solid-date drive, a flash drive, magnetic tape, or some other large capacity storage device. The storage device 330 may alternatively be a cloud storage device, e.g., a logical storage device including multiple physical storage devices distributed on a network and accessed using a network. In some embodiments, the information stored on the memory 320 can also or instead be stored on the storage device 330.

The input/output device 340 provides input/output operations for the system 300. In some embodiments, the input/output device 340 includes one or more of network interface devices (e.g., an Ethernet card), a serial communication device (e.g., an RS-232 port), and/or a wireless interface device (e.g., a short-range wireless communication device, an 802.11 card, a 3G wireless modem, or a 4G wireless modem). In some embodiments, the input/output device 340 includes driver devices configured to receive input data and send output data to other input/output devices, e.g., a keyboard, a printer, and display devices (e.g., such as the dosage window 113). In some embodiments, mobile computing devices, mobile communication devices, and other devices are used.

In some embodiments, the system 300 is a microcontroller. A microcontroller is a device that contains multiple elements of a computer system in a single electronics package. For example, the single electronics package could contain the processor 310, the memory 320, the storage device 330, and input/output devices 340.

Although an example processing system has been described in FIG. 3, embodiments of the subject matter and the functional operations described above can be embodiments in other types of digital electronic circuitry, or in computer software, firmware, or hardware, including the structures disclosed in this specification and their structural equivalents, or in combinations of one or more of them. Embodiments of the subject matter described in this specification can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the systems and techniques described herein have been presented. Nevertheless, it will be understood that various modifications may be made without departing from the spirit and scope of such system and techniques. Accordingly, other embodiments are within the scope of the following claims.

REFERENCE NUMERALS 100 injection device
102 cartridge
104a distal end
104b distal end
106 proximal end
108 first stopper
110 housing
111 injection button
112 dosage knob
113 dosage window
114 needle
115 second stopper
116 inner needle cap
117 outer needle cap
118 cap
119 aperture
120a reflector
120b reflector
122 transmitter
124 receiver
202 first electrode
204 second electrode
300 computer system
310 processor
320 memory
330 storage device
340 input/output device
350 system bus

The invention claimed is:

1. An injection device comprising:
   a cartridge configured to hold a volume of fluid, the cartridge having a proximal end and a distal end through which the fluid is dispensed;
   a first stopper disposed in the cartridge and configured to move from the proximal end toward the distal end to cause the fluid to be dispensed through the distal end of the cartridge;
   a second stopper disposed at the distal end of the cartridge, the second stopper comprising an aperture through which the fluid is dispensed, wherein the second stopper comprises a material that allows one or more waves and reflections of the one or more waves to pass therethrough;
   a reflector disposed at the distal end of the cartridge, wherein the reflector is embedded in the material of the second stopper; and
   a transmitter disposed in the first stopper, the transmitter being configured to transmit the one or more waves toward the reflector; and
   a receiver disposed in the first stopper, the receiver being configured to receive the reflections of the one or more waves from at least the reflector.

2. The injection device of claim 1, wherein the cartridge has a generally cylindrical shape that tapers into a cone shape at the distal end.

3. The injection device of claim 1, wherein the distal end of the cartridge comprises a bottom surface that forms a 90° angle with a peripheral wall of the cartridge.

4. The injection device of claim 3, wherein the reflector is disposed at the bottom surface such that the one or more waves are transmitted at normal incidence to the reflector.

5. The injection device of claim 1, wherein the cartridge comprises a material that allows the one or more waves and the reflections of the one or more waves to pass therethrough.

6. The injection device of claim 5, wherein the reflector is embedded in the material at the distal end of the cartridge.

7. The injection device of claim 5, wherein the reflector is disposed on an outer surface of the distal end of the cartridge.

8. The injection device of claim 1, wherein the transmitter is an acoustic transmitter and the one or more waves are acoustic waves.

9. The injection device of claim 1, wherein the transmitter is an optical source and the one or more waves are optical waves.

10. The injection device of claim 1, wherein the reflector is disposed on an inner surface of the distal end of the cartridge.

11. The injection device of claim 1, wherein the reflector is disposed on a surface of the second stopper.

12. The injection device of claim 1, comprising a transceiver that comprises the transmitter and the receiver.

13. The injection device of claim 1, wherein information related to the one or more waves and the reflections of the one or more waves is used to determine the volume of the fluid in the cartridge.

14. The injection device of claim 1, comprising the fluid held in the cartridge.

15. The injection device of claim 14, wherein the fluid comprises a medicament.

16. The injection device of claim 1, wherein the transmitter is an ultrasonic transmitter and the one or more waves are ultrasound waves.

17. An injection device comprising:
  a cartridge configured to hold a volume of fluid, the cartridge having a proximal end and a distal end through which the fluid is dispensed;
  a first stopper disposed in the cartridge and configured to move from the proximal end toward the distal end to cause the fluid to be dispensed through the distal end of the cartridge;
  a first electrode disposed in the first stopper;
  a second stopper disposed at the distal end of the cartridge, the second stopper comprising an aperture through which the fluid is dispensed; and
  a second electrode disposed on a surface of the second stopper facing the first electrode, wherein a voltage is applied across the first electrode and the second electrode, and a capacitance value related to the first electrode and the second electrode is indicative of a distance between the first stopper and the second stopper.

18. The injection device of claim 17, wherein the volume of the fluid in the cartridge is determined based on the distance between the first stopper and the second stopper.

* * * * *